United States Patent [19]

Kasai et al.

[11] Patent Number: 4,936,314
[45] Date of Patent: Jun. 26, 1990

[54] METHOD OF EVACUATING AND PRESERVING A BLOOD COLLECTING DEVICE

[75] Inventors: Masaaki Kasai, Zama; Yoshimitsu Asada; Kenji Ishikawa, both of Tokyo, Japan

[73] Assignee: Terumo Kabushiki Kaisha, Tokyo, Japan

[21] Appl. No.: 283,024

[22] Filed: Dec. 9, 1988

Related U.S. Application Data

[63] Continuation of Ser. No. 54,101, May 20, 1987, abandoned, which is a continuation of Ser. No. 736,417, May 20, 1985, abandoned, which is a continuation of Ser. No. 539,722, Oct. 6, 1983, abandoned.

[30] Foreign Application Priority Data

| Oct. 8, 1982 | [JP] | Japan | 176230 |
| Oct. 8, 1982 | [JP] | Japan | 176231 |
| Oct. 9, 1982 | [JP] | Japan | 178052 |

[51] Int. Cl.⁵ .......................... A61B 5/14; B65D 81/00
[52] U.S. Cl. ..................................... 128/764; 206/571; 206/438
[58] Field of Search ............... 128/760–767; 604/86, 201, 403, 408, 415; 206/571, 438; 435/298, 801

[56] References Cited

U.S. PATENT DOCUMENTS

| 2,283,867 | 5/1942 | Flosdorf et al. | 206/438 |
| 2,834,023 | 5/1958 | Lieb | 3/13 |
| 3,075,528 | 1/1963 | Lundgren et al. | 604/403 |
| 3,127,274 | 3/1964 | Weinke . | |
| 3,473,646 | 10/1969 | Burke | 206/571 |
| 3,901,219 | 8/1975 | Kay | 128/764 |
| 3,904,482 | 9/1975 | Mehl | 128/764 |
| 3,939,834 | 2/1976 | McMahon | 604/403 |
| 4,038,148 | 7/1977 | Miller et al. | 435/801 |
| 4,056,484 | 11/1977 | Heimburger et al. | 436/16 |
| 4,134,300 | 1/1979 | Svensson | 128/764 |
| 4,150,744 | 4/1979 | Fennimore | 206/363 |
| 4,197,947 | 4/1980 | Zaidi | 206/438 |
| 4,245,654 | 1/1981 | Raitto . | |
| 4,308,232 | 12/1981 | Crouther | 604/403 |
| 4,338,764 | 7/1982 | Percarpio . | |
| 4,419,451 | 12/1983 | Garner et al. | 435/298 |

FOREIGN PATENT DOCUMENTS

| 253889 | 9/1962 | Australia . |
| 12582 | 6/1976 | Australia . |
| 22251 | 8/1978 | Australia . |
| 0019940 | 12/1980 | European Pat. Off. . |
| 0059297 | 9/1982 | European Pat. Off. . |
| 54-35189 | 3/1979 | Japan . |
| 54-37088 | 3/1979 | Japan . |

Primary Examiner—Ruth S. Smith
Attorney, Agent, or Firm—Frishauf, Holtz, Goodman & Woodward

[57] ABSTRACT

An evacuated blood collecting device for collecting a blood sample of predetermined volume comprises: a cylindrical member having one open end and one closed end; a puncturable stopper member closing tightly the open end of the cylindrical member so as to seal the space within said cylindrical member; and a gas sealed in the space within the cylindrical member. The cylindrical member and the stopper member are made of materials having a characteristic such that the permeation coefficient of the gas sealed inside the space to at least one of the cylindrical member and stopper member is higher than that of the gas around the outside of the blood collecting device, whereby the interior of the space is retained under reduced pressure relative to the gas around the outside of the blood collecting device in proportion to the blood sampling volume.

6 Claims, 2 Drawing Sheets

METHOD OF EVACUATING AND PRESERVING A BLOOD COLLECTING DEVICE

This application is a continuation of Ser. No. 054,101, filed May 20, 1987 abandoned which is a continuation of Ser. No. 736,417 filed May 20, 1985 abandoned which in turn is a continuation of Ser. No. 539,722 filed Oct. 6, 1983 abandoned.

BACKGROUND OF THE INVENTION

1. Field of the Invention:

This invention relates to an evacuated blood collecting device and more particularly to an evacuated blood collecting device capable of protracted retention of a vacuum therein.

2. Description of Prior Art:

The method for collection of blood under a vacuum has found widespread acceptance because it entails hemolysis or coagulation only to a minimal extent and secures a blood sample hardly suffering from contamination or evaporation and, in terms of efficiency of work involved, simplifies preparations for blood collection and management of utensils. The evacuated blood-collecting device which is adopted for this method comprises a cylindrical receptacle and a puncturable rubber stopper for tightly sealing the cylindrical receptacle. The interior of the tightly sealed cylindrical receptacle is kept under a vacuum. This device effects desired collection of blood by having one end of a blood collection needle pierced into the blood vessel of a subject and the other end of the needle pierced through the rubber stopper into the receptacle thereby establishing communication between the blood vessel and the interior of the receptacle and enabling the blood to flow into the receptacle owing to the negative pressure in the receptacle. In the evacuated blood-collecting device of this type which has heretofore found utility in clinical applications, the cylindrical receptacle has been made of glass to meet the conditions of imperviousness to gas and high transparency and the stopper has been made of butyl rubber to meet the conditions of minimal perviousness to gas and high puncturability.

Unfortunately, the cylindrical receptacle made of glass has the disadvantage that it is liable to breakage during storage, transportation or actual use and it is heavy. Studies have been made, therefore in search for a cylindrical receptacle made of a synthetic resin featuring light weight and transparency, only to demonstrate that since every synthetic resin is more or less pervious to gas, the cylindrical receptacle made of any synthetic resin while in protracted storage permits the ambient gas such as, for example, air to pass into the tightly sealed evacuated blood collecting device and, as the result, the pressure within the syringe gradually rises possibly to the extent of making ineffectual the required blood collection under a vacuum. An attempt to adopt an evacuated blood collecting device made of a synthetic resin has inevitably necessitated use of a vacuum package to ensure safe preservation. The preservation by the use of a vacuum package, however, has the disadvantage of high cost because the package which by nature is required to keep its interior under a vacuum is very expensive and entails much time and labor when it is closed to seal its content when it is subsequently opened preparatory to putting the content to use.

Moreover, since the butyl rubber polymer which forms the basic material for the stopper of butyl rubber does not possess, in itself, properties necessitated by this particular product, it is inevitably required to undergo complicated steps such as the incorporation of adjuvants including sulfur and a vulcanization promotor. Further, the fabrication of the stopper using this polymer has the disadvantage of heavy loss of material because it gives rise to lots of burrs which cannot be reclaimed. Through incorporation of a thermoplastic elastomer, this polymer may be converted into a material capable of being reclaimed after molding. The stopper made of this modified polymer, however, has the disadvantage that it is more pervious to gas than the stopper made of butyl rubber.

SUMMARY OF THE INVENTION

An object of this invention, therefore, is to provide a novel evacuated blood collecting device. Another object of this invention is to provide an evacuated blood collecting device which is capable of protracted retention of a vacuum therein.

This invention attains these objects by an evacuated blood collecting device comprising a cylindrical member having one end thereof closed and the other end opened and a puncturable stopper member serving to close tightly the open end of the cylindrical member, the evacuated blood collecting device is characterized in that the device has a permeation coefficient of the gas inside the device to at least one of the component members of the device which is higher than that of the gas around the device. The interior of the device is thus retained under reduced pressure relative to the ambient gas in proportion to the blood sampling volume.

The evacuated blood collecting device mentioned above seals therein a gas to which the material of at least one of the two component members of the device exhibits a higher permeation coefficient than to the gas around the device and, at the same time, retains the interior thereof under reduced pressure relative to the ambient air.

The aforementioned objects of this invention are further attained by having the aforementioned device stowed in a tightly closed container. They are also attained by having the aforementioned device stowed in a tightly closed container in conjunction with a deoxidizer.

This invention, in one aspect, relates to an evacuated blood collecting device wherein the permeation coefficient to the material of at least one of the component members of the device is such that the permeation coefficient of the gas sealed in the device, taken as A, and the coefficient of the gas enveloping the device taken as B, satisfy the relationship $20 > A > 1.0$, preferably $10B > A > 4B$. This invention in another aspect relates to an evacuated blood collecting device wherein the gas sealed therein is at least one member selected from the group consisting of helium, argon, neon, oxygen, carbon dioxide, carbon monoxide, ethane and propane. This invention in still another aspect relates to an evacuated blood collecting device wherein the cylindrical member thereof is made of a synthetic resin. In yet another aspect, this invention relates to an evacuated blood collecting device wherein the synthetic resin is methyl methacrylate resin. In a further aspect, this invention relates to an evacuated blood collecting device wherein the stopper member thereof is made of a composition consisting of a thermoplastic elastomer, polyisobutylene and partially cross-linked butyl rubber.

The aforementioned objects of the present invention are further attained by having the aforementioned evacuated blood collecting device stowed in a tightly sealed container in conjunction with a deoxidizer and keeping the interior of the device under a vacuum.

This invention contemplates an evacuated blood collecting device wherein the cylindrical member thereof is made of a synthetic resin. It also contemplates an evacuated blood collecting device wherein the resin making up the cylindrical member thereof is methyl methacrylate resin. This invention further contemplates an evacuated blood collecting device wherein the stopper member thereof is made of a composition consisting of a thermoplastic elastomer, polyisobutylene and partially cross-linked butyl rubber.

PREFERRED EMBODIMENT OF THE INVENTION

Figure 1:
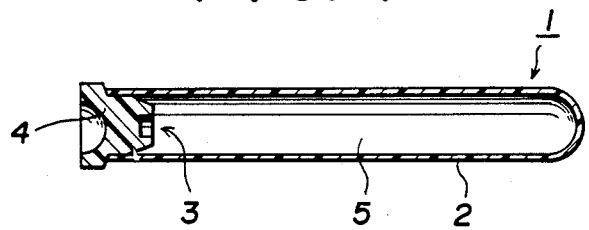
FIG. 1 is a cross section illustrating a typical evacuated blood-collecting device according to this invention.

As illustrated in FIG. 1, an evacuated blood collecting device 1 of this invention comprises a cylindrical member 2 having one end thereof closed and the other end opened and a puncturable stopper member 4 serving to seal tightly the open end 3 of the aforementioned cylindrical member 2. An inner space 5 of the tightly closed cylindrical member 2 contains a gas to which the materials of at least one of the two component members, i.e., the cylindrical member and the stopper member, of the device or the materials of both the component members exhibit higher permeation coefficients than to the gas enveloping the device and, at the same time, this inner space 5 is kept under reduced pressure relative to the ambient air.

Besides glass, the material making up the cylindrical member 2 may be a synthetic resin which exhibits a low degrees of permeability to gases, such as permeability to nitrogen not exceeding $1 \times 10^{-10}$ cm$^3$ (STP) cm/cm$^2$.sec.cmHg, preferably not exceeding $0.1 \times 10^{-10}$ (STP) cm/cm$^2$.sec.cmHg, excels in transparency, and possesses ample shape-retaining properties and mechanical strength. Typical examples of synthetic resins satisfying the requirement are polymethyl methacrylate, polyvinylidene chloride, polyvinyl chloride, ethylene-vinyl alcohol copolymer, polyethylene terephthalate, 6,6-nylon and 6-nylon. Among other synthetic resins, polymethyl methacrylate and ethylene-vinyl alcohol copolymer are particularly desirable. Polymethyl methacrylate is the most desirable synthetic resin. Besides butyl rubber, the material making up the stopper member 4 may be a substance which is desired to permit smooth penetration therethrough of a blood collection needle during the actual use of the syringe as will be described fully afterward, possess ample elasticity sufficient to preclude occurrence of a loose gap between the periphery of the blood collection needle penetrated therethrough and the inner wall of the puncture formed by this penetration in the stopper member, warrant reclamation when necessary, and exhibit as low degrees of permeability to gases as the aforementioned synthetic resin making up the cylindrical member. Typical examples of the substance satisfying the requirements are compositions consisting of thermoplastic elastomers, polyisobutylene and partially cross-linked butyl rubber, preferably a composition consisting of a thermoplastic elastomer, polyisobutylene and partially cross-linked butyl rubber.

The proportions of the components of the composition are 100 parts by weight of a thermoplastic elastomer taken as the basis, 100 to 200 parts by weight, preferably 120 to 150 parts by weight, of polyisobutylene and 100 to 200 parts by weight, preferably 120 to 150 parts by weight, of partially cross-linked butyl rubber.

Concrete examples of the thermoplastic elastomer are ethylene-propylene rubber composites, polyester elastomers, nylon elastomers, styrene-isoprene block copolymer, styrene-butadiene block copolymer, polybutadiene, thermoplastic polyurethane and hydrogenated styrene-butadiene block copolymer. The polyisobutylene is desired to have a molecular weight in the range of 15,000 to 200,000, preferably 80,000 to 150,000. The partially cross-linked butyl rubber is obtained by partially cross-linking butyl rubber which results from the copolymerization of isobutylene with a small proportion (0.3 to 3.0 mol %, for example) of isoprene.

The gas to be sealed in the inner space 5 of the evacuated blood collecting device 1 is required to be such that the permeation coefficient the cylindrical member or the stopper member of the device exhibits thereto is higher than that exhibited to the ambient gas enveloping the device. Particularly, the permeation coefficient exhibited to the gas sealed in the device taken as A and the permeation coefficient exhibited to the ambient gas taken as B are desired to satisfy the relationship 20B>A>1.0B, preferably 10B>A>4B.

Examples of the gas satisfying the requirement are helium, argon, neon, oxygen, carbon dioxide, carbon monoxide, ethane, propane, ethylene, propylene and butane. Among other gases, helium, argon, oxygen and carbon dioxide are particularly desirable. Argon and carbon dioxide are most desirable.

In the present invention, the gas such as defined above is sealed in the syringe for the following reason. When the gas thus sealed in the syringe is argon, for example, since the partial pressure of air (particularly the partial pressure of nitrogen) is substantially zero in the interior of the evacuated blood collecting device left standing under the atmospheric pressure, the atmospheric air (particularly nitrogen) permeates the device to increase the partial pressure of air (particularly of nitrogen) inside the device. With respect to the argon sealed in the device, since the partial pressure of argon in the atmosphere is virtually near zero, the argon inside the device permeates the device and diffuses into the ambient air. Moreover, since the speed at which the air (particularly nitrogen) permeates the device inwardly from the outside is lower than the speed at which the argon permeates the device outwardly from within the device, the total pressure within the device is not increased. Thus, the vacuum indispensable to the function of the device is safely retained. This situation similarly occurs where the evacuated blood collecting device is left standing under a blanket of nitrogen instead of under the atmosphere. If the gas sealed in the device is such that the permeation coefficient of the cylindrical member or the stopper member to that gas is excessively high, then the gas escapes from the device to an excessive extent, with a possible result that the vacuum inside the device will rise far more than is necessary and the blood will be drawn in far larger volume than required. Hence, the permeation coefficients exhibited to the gases inside and outside the device are required to satisfy the aforementioned relationship.

The vacuum inside the evacuated blood collecting device of this invention has only to satisfy the requirement that it provides negative pressure both necessary and sufficient for suction of a prescribed volume of blood into the device. When the evacuated blood collecting device has an inner volume of 12 ml, for example, it suffices for the collection of 10 ml of blood to evacuate the interior of the device until the gas pressure falls to $76 \times (2/12)$ cmHg. Of course, an anticoagulative agent may be contained in advance in the evacuated blood-collecting device as occasion demands.

The evacuated blood collecting device constructed as described above is put to use as follows. The evacuated blood collecting device 1 which has a prescribed gas sealed therein and which has the interior thereof evacuated to a prescribed degree as illustrated in FIG. 1 is posed in front of a device holder 9 which has one end thereof closed and the other end opened and has a blood collection needle 8 helically fastened to a threaded hole 7 formed in the closed end 6. Then, the device 1 is inserted into the device holder 9 through the aforementioned opened end thereof. The blood collection needle 8 comprises a blood vessel piercing portion 8a and a stopper piercing portion 8b, for example. The stopper piercing portion 8b is wrapped in a Luer adapter 10. Then, the blood vessel piercing portion 8a of the blood collection needle 8 is pierced into the blood vessel such as, for example, the vein and the evacuated blood-collecting device 1 is urged into the closed end portion 6 of the device holder 9 until the stopper piercing portion 8b of the blood-collection needle 8 pierces through the Luer adapter 10 and the stopper member 4 and the leading tip thereof reaches the inner space 5 of the device 1. Consequently, the inner space 5 is allowed to communicate with the blood vessel. Owing to the negative pressure existing in the inner space 5, the blood in the blood vessel blows into the inner space 5 of the device 1 in a total volume corresponding to the degree of the vacuum in the device 1. The collection of blood is terminated by removing the blood vessel piercing portion 8a of the blood-collection needle 8 from the blood vessel.

The aforementioned evacuated blood collecting device offers better results when it is preserved as stowed in a tightly sealing container.

Figure 4:
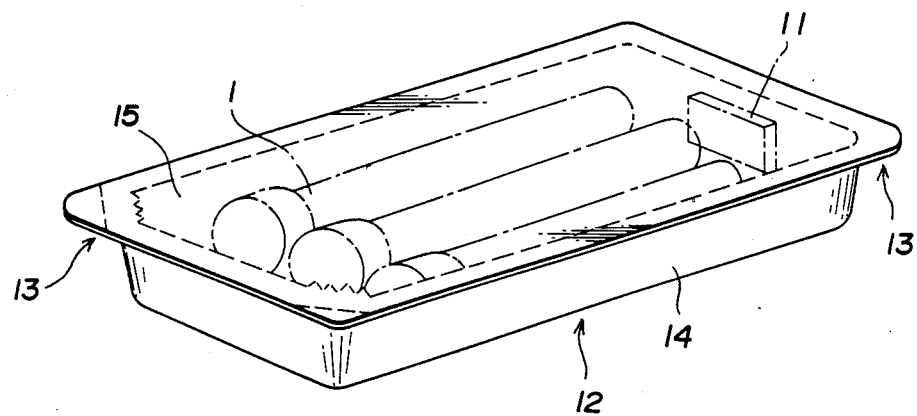
FIG. 4 is a perspective view illustrating the evacuated blood collecting device stowed in a tightly closed container.

The tightly sealing container 12 for use in this invention fulfils its function solely by possessing an ability to barrier flow of a gas therethrough and never by possessing any particular shape. As illustrated in FIG. 4, for example, it may comprise a container body 14 resembling a rectangular plate and having a flange 13 formed along the upper periphery of the container body 14 and a sheet cover 15 having the peripheral edge thereof heat sealed peel-openably through the medium of hotmelt to the aforementioned flange 13. Of course, a blister package is also useful as the tightly sealing container 12.

The material possessing a gas barriering property high enough for the purpose of the tightly sealing container 12 is required to exhibit oxygen gas permeability of not more than $0.1 \times 10^{-10}$ cm$^3$ (STP) cm/cm$^2$.sec.cmHg, preferably not more than $0.001 \times 10^{-10}$ cm$^3$ (STP) cm/cm$^2$.sec.cmHg. Examples of the material fulfilling this requirement are a laminate of biaxially stretched polypropylene, ethylene-vinyl alcohol copolymer, and biaxially stretched polypropylene, a laminate of ethylene-vinyl alcohol copolymer and polyethylene, a laminate of polyvinylidene chloride and polyethylene, and laminate of polypropylene, ethylene-vinyl alcohol copolymer and polypropylene. The total thickness of any of these laminates is in the range of 50 to 1500 $\mu$m, preferably in the range of 100 to 1000 $\mu$m.

Various deoxidizers are available. For example, an oxygen absorbent composed of a metal halide (optionally containing water) and at least one compound selected from the group consisting of iron carbide, carbonyl iron, ferrous oxide, ferrous hydroxide and ferrosilicon (Published Unexamined Japanese Patent Application SHO No. 54(1979)-37088) and an oxygen absorbent formed by coating powdered metal with a metal halogenide (Published Unexamined Japanese Patent Application SHO No. 54(1979)-35189).

Required tight sealing of the device 1 in the container 12 constructed as described above is effected by placing the device 1 in conjunction with the deoxidizer, which is optionally used, in the plate-shaped container body 14, then applying the lid 15 through the medium of hotmelt to the flange 13, and heat sealing the container body and the lid.

This invention contemplates sealing the gas defined above in the device preserved in conjunction with the deoxidizer in the container for the following reason. Where the gas to be sealed in the device is argon, for example, if the evacuated blood-collecting device is preserved in conjunction with the deoxidizer in the tightly sealing container, then nitrogen exists substantially along in the interior of the tightly sealing container. In this case, since the partial pressure of nitrogen inside the device is substantially zero, the nitrogen in the tightly sealing container permeates the device and the partial pressure of nitrogen inside the device increases. With respect to the argon contained in the device, since the partial pressure of argon inside the tightly sealing container is virtually near zero, the argon in the device permeates the device outwardly and diffuses in the interior of the tightly sealing container. Moreover, since the speed at which nitrogen permeates device inwardly from outside is lower than the speed at which argon permeates the device outwardly from inside, the total pressure within the device is not increased. Thus, the vacuum necessary for the function of the device is maintained intact. Further, nitrogen has less permeation coefficient compared to air, so increase of the total pressure in the blood collecting device can be gentle. If the permeation coefficient of the device to the gas entrapped therein is excessively high, the sealed gas escapes excessively from the device and the device is caused to draw blood more than is necessary. Hence, the permeation coefficients of the device to the gases inside and outside are desired to fall within the range defined by the aforementioned formula.

Figure 2:
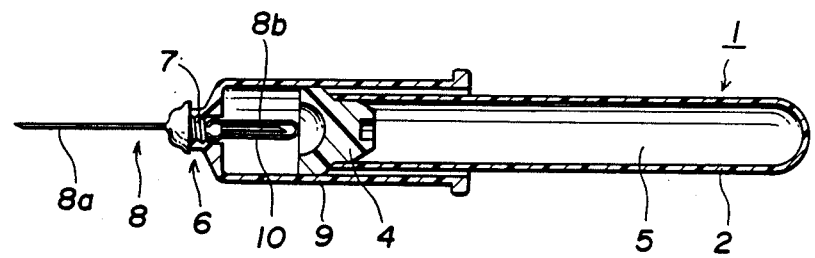
FIG. 2 and FIG. 3 are cross section illustrating conditions under which the evacuated blood collecting device is used.
Figure 3:
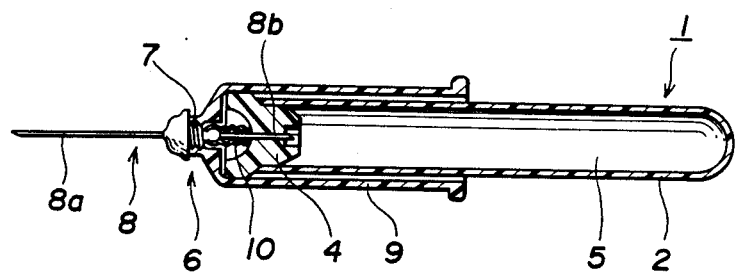

The degree of vacuum required to be retained in the evacuated blood-collecting device of this invention is as already described above. From the tightly sealing container 12 illustrated in FIG. 4, the evacuated blood collecting device 1 constructed as described above and having the prescribed gas sealed therein to a prescribed degree of vacuum is remove peeling the lid 15 off the container 12. It is then put to use by following the same procedure as used for the evacuated blood-collecting device illustrated in FIG. 2 and FIG. 3.

In another embodiment of this invention, the evacuated blood-collecting device is stowed in the tightly sealing container 12 in conjunction with the deoxidizer 11 as illustrated in FIG. 4. In this case, the evacuated blood collecting device 1 has a gas such as air, preferably a gas containing oxygen, sealed in the inner space 5 thereof and, at the same time, retains the inner space 5 under reduced pressure relative to the ambient gas.

The cylindrical member of the device 1 and the tightly sealing container 12 are formed of materials defined above and in constructions similarly defined above.

Figure 5:
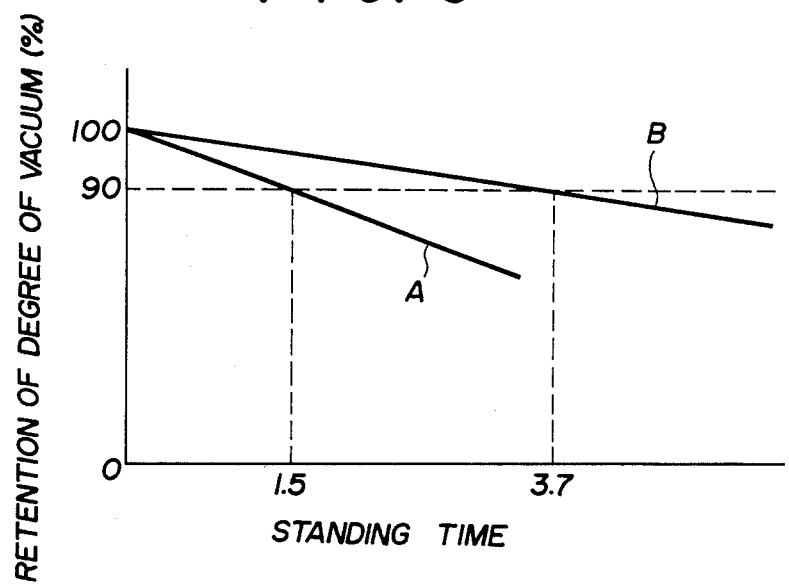
FIG. 5 is a graph showing a time-course change of the degree of vacuum maintained inside the evacuated blood collecting device.

In the present invention, the device seals the prescribed gas therein and it is stowed in conjunction with the deoxidizer within the tightly sealing container for the following reason. In the absence of the tightly sealing container and the deoxidizer, air (oxygen and nitrogen) permeates the device and diffuses in the inner space and, consequently, the degree of vacuum inside the device is rapidly lowered (as indicated by the straight line A in FIG. 5). In accordance with the present invention, since the presence of oxygen in the tightly sealing container is substantially eliminated by the action of the deoxidizer, the otherwise possible passage of oxygen from the gas in the tightly sealing container into the inner space of the device is precluded. Thus, the retention of the degree of vacuum inside the device is proportionately protracted. Further, the fact that oxygen present in the device passes conversely into the tightly sealing container adds much to the protracted retention of the degree of vacuum (as indicated by the straight line B in FIG. 5).

As described above, the tightly sealed container is not always required to be impervious to gas. It is allowed to fulfil its function satisfactorily when the amount of the oxygen absorbent contained therein is adjusted in proportion to the container's permeability to oxygen.

The evacuated blood collecting device of the present invention is capable of retaining the degree of vacuum as described above. It is put to use by the method already described above.

Now, the present invention will be described more specifically below with reference to working examples.

EXAMPLE 1

A cylindrical receptacle 2 having one end thereof closed and the other end opened as illustrated in FIG. 1 and having a wall thickness of 1 mm was formed of polymethyl methacrylate. Separately, a stopper member 4 was formed of a composition consisting of 25 parts by weight of a thermoplastic elastomer (1,2-polybutadiene), 35 parts by weight of polyisobutylene (molecular weight 100,000), 25 parts by weight of partially crosslinked butyl rubber, and 15 parts by weight of liquid paraffin. This stopper member was tightly fitted in the open end 3 of the cylindrical receptacle 2, with argon sealed in and retained at a vacuum (inner pressure) of 150 mmHg in the cylindrical receptacle 2. Under the conditions, the polymethyl methacrylate forming the cylindrical receptacle showed a permeation coefficient of $0.5 \times 10^{-10}$ cm$^3$ (STP) cm/cm$^2$.sec.cmHg to argon and a permeation coefficient of $0.2 \times 10^{-10}$ cm$^3$ (STP) cm/cm$^2$.sec. cmHg to air. Samples of the evacuated blood collecting device 1 constructed as described above were left standing under atmosphere for varying lengths of time and tested for time-course change in the volume of blood collected. The results were as shown in Table 1.

EXAMPLES 2-5

The procedure of Example 1 was repeated, except that oxygen, carbon dioxide, helium and carbon monoxide were respectively used as sealing gas in the place of argon. The results were as shown in Table 1.

Control 1

The procedure of Example 1 was repeated, except that air was used as sealing gas in the place of argon. The results were as shown in Table 1.

TABLE 1

| | | Volume of blood collected (ml) | | | |
| | | Immediately after production | After lapse of | | |
| Samples | Sealed gas | | One year | Two years | Three years |
|---|---|---|---|---|---|
| Example 1 | Argon | 10.0 | 9.3 | 8.6 | 8.0 |
| Example 2 | Oxygen | 10.0 | 9.5 | 9.0 | 8.6 |
| Example 3 | Carbon dioxide | 10.0 | 10.0 | 9.6 | 8.5 |
| Example 4 | Helium | 10.0 | 11.0 | 9.8 | 8.6 |
| Example 5 | Carbon monoxide | 10.0 | 10.0 | 9.6 | 8.5 |
| Control 1 | Air | 10.0 | 8.8 | 7.7 | 6.7 |

When these experiments were repeated with samples using stopper members made of butyl rubber, the results were similar to those indicated above.

EXAMPLE 6

A cylindrical receptacle 2 having one end closed and the other end opened as illustrated in FIG. 1 and having a wall thickness of 1 mm was formed of glass. Separately, a stopper member 4 was formed of a thermoplastic elastomer (solely of 1,2-polybutadiene). The stopper member was tightly fitted into the open end 3 of the aforementioned cylindrical receptacle 2, with argon sealed in and retained at a vacuum (inner pressure) of 150 mmHg in the cylindrical receptacle. Under the conditions, the 1,2-polybutadiene forming the cylindrical receptacle exhibited a permeation coefficient of $41.1 \times 10^{-10}$ cm$^3$ (STP) cm/cm$^2$.sec.cmHg and a permeation coefficient of $16.5 \times 10^{-10}$ cm$^3$ (STP) cm/cm$^2$.sec.cmHg to air. Samples of the evacuated blood collecting device 1 constructed as described above were left standing under atmosphere for varying lengths of time and tested for time-course change in the volume of blood collected. The results were as shown in Table 2.

Examples 7-10

The procedure of Example 6 was repeated, except that oxygen, carbon dioxide, helium and carbon monoxide were respectively used in the place of argon. The results were as shown in Table 2.

Control 2

The procedure of Example 6 was repeated, except that air was used in the place of argon. The results were as shown in Table 2.

TABLE 2

| Samples | Sealed gas | Volume of blood collected (ml) | | | |
|---|---|---|---|---|---|
| | | Immediately after production | After lapse of | | |
| | | | One year | Two years | Three years |
| Example 6 | Argon | 10.0 | 9.0 | 8.1 | 7.3 |
| Example 7 | Oxygen | 10.0 | 9.3 | 8.6 | 8.0 |
| Example 8 | Carbon dioxide | 10.0 | 9.9 | 9.4 | 8.3 |
| Example 9 | Helium | 10.0 | 10.0 | 9.3 | 8.2 |
| Example 10 | Carbon monoxide | 10.0 | 9.7 | 9.2 | 8.2 |
| Control 2 | Air | 10.0 | 8.5 | 7.0 | 5.6 |

EXAMPLE 11

An evacuated blood collecting device 1 obtained by the procedure of Example 1 was stowed in a container 12 as illustrated in FIG. 4, with a lid 15 applied through the medium of hotmelt to a flange 13 and heat sealed. Under the conditions, the polymethyl methacrylate forming the cylindrical receptacle exhibited a permeation coefficient of $0.5 \times 10^{-10}$ cm$^3$ (STP) cm/cm$^2$.sec.cmHg to argon and a permeation coefficient of $0.2 \times 10^{-10}$ cm$^3$ (STP) cm/cm$^2$.sec.cmHg to air. Samples of the evacuated blood collecting device 1 constructed as described above were left standing under atmosphere by way of test for the time-course change in the volume of blood extracted. The results were as shown in Table 3.

EXAMPLE 12-15

The procedure of Example 11 was repeated, except that oxygen, carbon dioxide, helium and carbon monoxide were respectively used in the place of argon. The results were as shown in Table 3.

CONTROL 3

The procedure of Example 11 was repeated, except that air was used in the place of argon. The results were as shown in Table 3.

TABLE 3

| Samples | Sealed gas | Volume of blood collected (ml) | | | |
|---|---|---|---|---|---|
| | | Immediately after production | After lapse of | | |
| | | | One year | Two years | Three years |
| Example 11 | Argon | 10.0 | 9.2 | 8.5 | 7.8 |
| Example 12 | Oxygen | 10.0 | 9.4 | 8.9 | 8.4 |
| Example 13 | Carbon dioxide | 10.0 | 10.0 | 9.6 | 8.7 |
| Example 14 | Helium | 10.0 | 10.8 | 9.6 | 8.5 |
| Example 15 | Carbon monoxide | 10.0 | 10.0 | 9.5 | 8.4 |
| Control 3 | Air | 10.0 | 8.8 | 7.7 | 6.7 |

When these experiments were repeated with samples using stopper members made of butyl rubber, the results were similar to those indicated above.

EXAMPLE 16-20

The procedures of Example 11-15 were repeated, except that "Ageless" (trademark designation of a product of Mitsubishi Gas Chemical Company, Ltd.) was stowed in tightly sealing containers as a deoxidizer in conjunction with evacuated blood collecting device 1. Samples of the evacuated blood collecting device 1 constructed as described above were tested for time-course change in the volume of blood collected. The results were as shown in Table 4.

Control 4

The procedure of 16 was repeated, except that air was used in the place of argon. The results were as shown in Table 4.

TABLE 4

| Samples | Sealed gas | Volume of blood collected (ml) | | | |
|---|---|---|---|---|---|
| | | Immediately after production | After lapse of | | |
| | | | One year | Two years | Three years |
| Example 16 | Argon | 10.0 | 9.6 | 9.3 | 9.0 |
| Example 17 | Oxygen | 10.0 | 9.4 | 8.9 | 9.2 |
| Example 18 | Carbon dioxide | 10.0 | 10.0 | 9.8 | 9.4 |
| Example 19 | Helium | 10.0 | 11.0 | 9.7 | 9.5 |
| Example 20 | Carbon monoxide | 10.0 | 10.0 | 9.8 | 9.4 |
| Control 4 | Air | 10.0 | 9.3 | 8.6 | 8.0 |

When these experiments were repeated with samples using stopper members made of butyl rubber, the results were similar to those indicated above.

EXAMPLE 21

An evacuated blood collecting device 1 obtained by the procedure of Example 6 was stowed in a container 12 as illustrated in FIG. 4, with a lid 15 hot sealed through the medium of hotmelt to a flange 13. Under the conditions, the 1,2-polybutadiene forming the stopper member exhibited a permeation coefficient of $41.0 \times 10^{-10}$ cm$^3$ (STP) cm/cm$^2$.sec.cmHg to argon and a permeation coefficient of $16.5 \times 10^{-10}$ cm$^3$ (STP) cm/cm$^2$.sec.cmHg to air. Samples of the evacuated blood collecting device 1 constructed as described above were left standing under atmosphere by way of test for time-course change in the volume of blood collected. The results were as shown in Table 5.

Examples 22-25

The procedure of Example 21 was repeated, except that oxygen, carbon dioxide, helium and carbon monoxide were used in the place of argon. The results were as shown in Table 5.

Control 5

The procedure of Example 21 was repeated, except that air was used in the place of argon. The results were as shown in Table 5.

TABLE 5

| Samples | Sealed gas | Volume of blood collected (ml) | | | |
|---|---|---|---|---|---|
| | | Immediately after production | After lapse of | | |
| | | | One year | Two years | Three years |
| Example 21 | Argon | 10.0 | 8.9 | 8.0 | 7.2 |
| Example 22 | Oxygen | 10.0 | 9.2 | 8.4 | 7.8 |
| Example 23 | Carbon dioxide | 10.0 | 9.8 | 9.4 | 8.4 |
| Example 24 | Helium | 10.0 | 10.3 | 9.2 | 8.1 |
| Example 25 | Carbon monoxide | 10.0 | 9.6 | 9.1 | 8.1 |
| Control 5 | Air | 10.0 | 8.5 | 7.0 | 5.6 |

Example 26-30

The procedures of Examples 21-25 were repeated, except that "Ageless" (trademark designation of a product of Mitsubishi Gas Chemical Company, Ltd.) was stowed in the tightly sealing containers as a deoxidizer in conjunction with the evacuated blood-collecting device 1. Samples of the evacuated blood collecting device 1 constructed as described above were tested for timecourse change in the volume of blood collected. The results were as shown in Table 6.

Control 6

The procedure of Example 26 was repeated, except that air was used in the place of argon. The results were as shown in Table 6.

TABLE 6

| Samples | Sealed gas | Volume of blood collected (ml) | | | |
|---|---|---|---|---|---|
| | | Immediately after production | After lapse of | | |
| | | | One year | Two years | Three years |
| Example 26 | Argon | 10.0 | 9.2 | 8.5 | 7.8 |
| Example 27 | Oxygen | 10.0 | 9.4 | 8.9 | 8.3 |
| Example 28 | Carbon dioxide | 10.0 | 10.0 | 9.7 | 9.3 |
| Example 29 | Helium | 10.0 | 10.6 | 10.2 | 9.8 |
| Example 30 | Carbon monoxide | 10.0 | 9.8 | 9.5 | 9.2 |
| Control 6 | Air | 10.0 | 9.0 | 8.4 | 7.8 |

EXAMPLE 31

A cylindrical receptacle obtained by the procedure of Example 1 had its open end 3 tightly sealed, with the interior of the cylindrical receptacle 2 evacuated under the blanket of air to a vacuum (inner pressure) of 150 mmHg. The evacuated blood-collecting device 1 thus obtained was stowed in a container 12 as illustrated in FIG. 4 in conjunction with "Ageless" (trademark designation of Mitsubishi Gas Chemical Co., Ltd.) as a deoxidizer. Than, a lid 15 was heat sealed through the medium of hotmelt to a flange 13. The polymethyl methacrylate forming the cylindrical receptacle exhibited a permeation coefficient of $1.15 \times 10^{-10}$ cm$^3$ (STP) cm/cm$^2$.sec. cmHg to oxygen and a permeation coefficient of $0.22 \times 10^{-10}$ cm$^3$ (STP) cm/cm$^2$.sec.cmHg to nitrogen. The container 12 and the lid 15 were both made of a laminate film formed of biaxially stretched polypropylene film (30 μm in thickness), ethylene-vinyl alcohol copolymer film (15 μm in thickness) and a non-stretched polypropylene film (30 μm in thickness). The vacuum bloodextraction syringe 1 thus obtained was tested for time-course change in the volume of blood collected. The results were as shown in Table 7.

Control 7

The procedure of Example 31 was repeated, except that the use of the deoxidizer and that of the tightly sealing container were both oxitted. The results were as shown in Table 7.

TABLE 7

| Samples | Volume of blood collected (ml) | | | |
|---|---|---|---|---|
| | Immediately after production | After lapse of | | |
| | | one year | Two years | Three years |
| Example 31 | 10.0 | 9.8 | 9.5 | 9.2 |
| Control 7 | 10.0 | 8.8 | 7.7 | 6.7 |

When these experiments were repeated with samples using stopper members made of butyl rubber, the results were similar to those indicated above.

EXAMPLE 32

A cylindrical receptacle 2 having one end closed and the other end opened as illustrated in FIG. 1 and having a wall thickness of 1 mm was made of glass. Separately, a stopper member 4 was made of a thermoplastic elastomer (solely of 1,2-polybutadiene). The stopper member was tightly fitted into the open end 3 of the cylindrical receptacle 2, with the interior of the cylindrical receptacle 2 evacuated under the blanket of air to a vacuum (inner pressure) of 150 mmHg. The evacuated blood collecting device 1 obtained as described above was stowed in a container 12 as illustrated in FIG. 4, with a lid 15 heat sealed through the medium of hotmelt to a flange 13. Under the conditions, the 1,2-polybutadiene forming the stopper member exhibited a permeation coefficient of $19.0 \times 10^{-10}$ cm$^3$ (STP) cm/cm$^2$.sec.cmHg to oxygen and a permeation coefficient of $6.42 \times 10^{-10}$ cm$^3$ (STP) cm/cm$^2$.sec.cmHg to air. The container 12 and the lid 15 were both made of a laminate film formed of a biaxially stretched polypropylene film (30 μm in thickness), an ethylene-vinyl alcohol copolymer film (15 μm in thickness), and a non-stretched polypropylene film (30 μm in thickness). The evacuated blood collecting device 1 thus produced was tested for time-course change in the volume of blood collected. The results were as shown in Table 8.

CONTROL 8

The procedure of Example 32 was repeated, except that the use of the deoxidizer and that of the tightly sealing container were both omitted. The results were as shown in Table 8.

TABLE 8

| Samples | Volume of blood collected (ml) | | | |
|---|---|---|---|---|
| | Immediately after production | After lapse of | | |
| | | one year | Two years | Three years |
| Example 32 | 10.0 | 9.7 | 9.3 | 8.8 |
| Control 8 | 10.0 | 8.5 | 7.0 | 5.6 |

What is claimed is:

1. A method of evacuating and preserving a blood collecting device which is used for collecting a blood sample of predetermined volume, wherein the amount of blood collectible by said blood collecting device is reduced by no more than about 10% per year,
the blood collecting device comprising a cylindrical member having one open end and one closed end, and defining a space therein; and a puncturable stopper member sealing the space within said cylindrical member;
the method comprising: sealing a first gas in said space within said cylindrical member under a reduced pressure relative to a second gas surrounding the outside of said cylindrical member, and creating a desired reduced pressure in said space as is necessary and sufficient for suction of said predetermined volume of blood into the device;
making said cylindrical member of synthetic resin materials having a permeability to nitrogen not exceeding $0.1 \times 10^{-10}$ (STP) cm/cm$^2$. sec.cmHg and a gas permeation characteristic such that the permeation coefficient of said first gas sealed inside said space of said cylindrical member is higher than that of said second gas surrounding the outside of said blood collecting device, and retaining the interior of said space under reduced pressure relative to said second gas surrounding the outside of said blood collecting device by selectively maintaining different permeation rates of said first and said second gases through the cylindrical member;

enclosing said blood collecting device, having said reduced pressure first gas sealed within said space, in a container for storage, and tightly sealing said second gas in said container in surrounding relation to the outside of said blood collecting device, said tightly sealed container having no gas generating device therein, and being made of a material serving as a barrier to a flow of gas therethrough;

causing said gas permeation characteristic of the material of said cylindrical member to be such that the permeation coefficient of said first gas sealed in said space, taken as A, and the permeation coefficient of said second gas surrounding the outside of said blood collecting device, taken as B, satisfies the relationship $20B > A > 1.0B$ when the device is enclosed in said tightly sealed container ; and permitting said first gas sealed in said space of said cylindrical member to permeate to the outside of said cylindrical member through said cylindrical member, and permitting said second gas surrounding the outside of said cylindrical member and inside of said tightly sealed container to permeate to the interior of said cylindrical member through said cylindrical member at such respective permeation rates as to maintain said reduced pressure in said cylindrical member, thereby preserving the desired reduced pressure for said blood collecting device .

2. The method according to claim 1, further comprising placing a deoxidizer in said tightly sealed container.

3. The method according to claim 1, comprising making said tightly sealed container of synthetic resin possessing a gas barrier property.

4. The method according to claim 3, comprising making said synthetic resin of said tightly sealed container of a material which exhibits an oxygen gas permeability of not more than $0.1 \times 10^{-10}$ cm3 (STP) cm/cm2.sec.cmHg.

5. The method according to claim 3, comprising making said synthetic resin of said tightly sealed container of a material which exhibits an oxygen gas permeability of not more than $0.001 \times 10^{-10}$ cm$^3$ (STP) cm/cm2.sec.cmHg.

6. The method according to claim 1, wherein said step of sealing said first gas in said space within said cylindrical member comprises sealing argon gas as said first gas inside said space of said cylindrical member; and further comprising sealing nitrogen gas as said second gas in said tightly sealed container.

7. The method according to claim 1, wherein said step of sealing said first gas in said space within said cylindrical member comprises sealing air as said first gas inside said space of said cylindrical member; and further comprising sealing nitrogen gas as said second gas in said tightly sealed container.

* * * * *

UNITED STATES PATENT AND TRADEMARK OFFICE
CERTIFICATE OF CORRECTION

PATENT NO. : 4,936,314
DATED : June 26, 1990
INVENTOR(S) : KASAI et al It is certified that error appears in the above-identified patent and that said Letters Patent is hereby corrected as shown below:

Column 1, line 65, after "content", insert --and--.

Column 1, line 68 (last line), delete "of butyl rubber".

Column 2, lines 25-26, change "member, the" to --member. The--.

Column 6, line 68 (last line), change "remove" to --removed by--.

Column 11, line 55, change "oxitted" to --omitted--.

Column 12, line 59 (claim 1), change "sad" to --said--.
Title Page:
Below Abstract, change "6 Claims, 2 Drawing Sheets" to --7 Claims, 2 Drawing Sheets--.

Signed and Sealed this

Ninth Day of June, 1992

*Attest:*

DOUGLAS B. COMER

*Attesting Officer*   *Acting Commissioner of Patents and Trademarks*